(12) United States Patent
Hanaway et al.

(10) Patent No.: US 8,541,180 B1
(45) Date of Patent: Sep. 24, 2013

(54) COMPOSITIONS AND METHODS FOR ASSESSING GASTROINTESTINAL HEALTH

(75) Inventors: Patrick Hanaway, Weaverville, NC (US); Jeffrey Ledford, Fletcher, NC (US)

(73) Assignee: Genova Diagnostics, Inc., Asheville, NC (US)

( * ) Notice: Subject to any disclaimer, the term of this patent is extended or adjusted under 35 U.S.C. 154(b) by 97 days.

(21) Appl. No.: 12/901,967

(22) Filed: Oct. 11, 2010

(51) Int. Cl.
*G01N 33/53* (2006.01)

(52) U.S. Cl.
USPC .............................................. 435/7.1; 435/7.2

(58) Field of Classification Search
None
See application file for complete search history.

(56) References Cited

U.S. PATENT DOCUMENTS

| | | |
|---|---|---|
| 5,716,791 A | 2/1998 | Larka et al. |
| 5,871,942 A | 2/1999 | Larka et al. |
| 5,932,430 A | 8/1999 | Larka et al. |
| 2006/0188939 A1* | 8/2006 | Gao .............................. 435/7.1 |

OTHER PUBLICATIONS

Rhoads et al. (J. Pediatr 2009 vol. 155, p. 823-8).*
Stein et al. (Clinical Chem. 1996 vol. 42, p. 222-226).*
Hanaway, "Irritable Bowel Syndrome: An Integrated Aproach to 'Gut Feelings'", Integrative Med. 3(5):16-21, 2004.
Hanaway, "Balance of Flora, Galt, and Mucosal Integrity", Alternative Therapies 12(5):52-60, 2006.
Hanaway, "Ask the Experts", Explore 2(3):284, 2006.
Katanik et al., "Evaluation of ColorPAC *Giardia/Cryptosporidium* Rapid Assay and ProSpecT *Giardia/Cryptosporidium* Microplate Assay for Detection of *Giardia* and *Cryptosporidium* in Fecal Specimens", J. Clin. Microbiol. 39(12):4523-4525, 2001.
Kligler et al., "Probiotics in Children", Pediatr. Clin. N. Am. 54:949-967, 2007.
Sult, "Clinical Approaches to Gastrointestinal Imbalance" In Textbook of Functional Medicine, Chapter 28, pp. 441-486, ed. D. Jones and S. Quinn, Gig Harbor, WA, 2005.
Product Insert, Premier Platinum HpSA (RTM) Plus "Enzymer Immunoassay for the Detection of Helicobacter pylori Antigens in Stool Specimens for Diagnosis and Monitoring", 2008.

* cited by examiner

*Primary Examiner* — Jacob Cheu
(74) *Attorney, Agent, or Firm* — Duane Morris, LLP; Lee Crews

(57) ABSTRACT

The present invention relates to kits designed for the collection of stool samples and methods of analyzing those samples for biological markers of maldigestion, inflammation, and imbalanced gut flora.

9 Claims, 3 Drawing Sheets

FIG. 3

Patient: SAMPLE PATIENT
Age: 34
Sex: F
MRN:

Order Number:
Completed:
Received:
Collected:

IBStatus Components

| Maldigestion: | | Reference Range |
|---|---|---|
| Pancreatic Elastase | 260 | >=201 mcg/g |

| Inflammation: | | Reference Range |
|---|---|---|
| Calprotectin | 125 | <=50 mcg/g |
| Occult Blood | Negative | Negative |

| Infection: | | Reference Range |
|---|---|---|
| Clostridium difficile | Negative | Negative |
| Parasitology Microscopic Exam: | No Ova or Parasites seen | |

| Parasitology EIA Tests: | | Reference Range |
|---|---|---|
| *Cryptosporidium* | Negative | Negative |
| *Giardia lamblia* | Negative | Negative |
| *E. histolytica* | Negative | Negative |
| EIA Test: *Helicobacter pylori* | Positive | Negative |

| Food Allergy: | | Reference Range |
|---|---|---|
| * Eosinophil Protein X | 0.5 | <=7.0 mcg/g |

Assays noted with * are For Research Use Only.

Commentary is provided to the practitioner for educational purposes, and should not be interpreted as diagnostic or treatment recommendations. Diagnosis and treatment decisions are the responsibility of the practitioner.

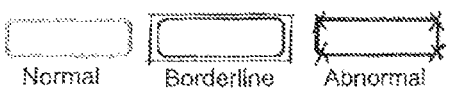

Key: Normal  Borderline  Abnormal

COMPOSITIONS AND METHODS FOR ASSESSING GASTROINTESTINAL HEALTH

FIELD OF THE INVENTION

The present invention relates to kits designed for the collection of stool samples and methods of analyzing those samples for biological markers of maldigestion, inflammation, and imbalanced gut flora.

BACKGROUND

Irritable bowel syndrome (IBS) is a functional disorder of the intestine characterized by altered bowel function (diarrhea, constipation, or both) and abdominal pain. It is the most common gastrointestinal disorder seen in general practice, and the prevalence of IBS has been estimated to be as high as 20% of the general population of North America. The majority of IBS sufferers are women, and women account for 80% of the cases of severe IBS.

SUMMARY

The methods described herein offer a concise look at the overall health of a patient's gastrointestinal (GI) tract. They include a number of non-invasive tests that evaluate digestion, inflammation, and gut flora. The outcome of these tests can assist in the diagnosis and treatment of IBS. Accordingly, in one aspect, the invention features methods of assessing a patient's gastrointestinal health by providing a stool sample from the patient and subjecting the sample to three tests: a first test for maldigestion, a second test for inflammation, and a third test for gut flora. Testing for maldigestion can include assessments of digestion and/or absorption of nutrients from the GI tract. For example, the first test for maldigestion can include testing for pancreatic insufficiency by evaluating the amount (e.g., the concentration) of a pancreatic elastase (PE), or a heterologous protein that is co-regulated with PE, in the stool sample. The PE can be the isozyme pancreatic elastase 1 (PE1). Concentrations of PE1 that are more than about 200 µg per gram of stool, but less than about 350 µg per gram of stool, indicate mild pancreatic insufficiency; concentrations of more than about 100 µg of PE1 per gram of stool, but less than about 200 µg of PE1 per gram of stool, indicate moderate pancreatic insufficiency; and concentrations of less than about 100 µg of PE1 per gram of stool indicate severe pancreatic insufficiency. When desired (e.g., when pancreatic insufficiency is moderate to severe), the methods can also include a step of testing for intestinal permeability, generating a comprehensive parasitology profile, and/or testing for Celiac disease. When desired (e.g., when pancreatic insufficiency is moderate to severe), the methods can also include a step of assessing bone resorption, analyzing glucose and/or insulin levels, testing for Celiac disease, and/or testing for bacterial overgrowth in the small intestine.

The second test, for inflammation, can be carried out by testing for calprotectin or occult blood in the stool sample. The testing for calprotectin can be carried out by evaluating the amount of calprotectin (e.g. its concentration), or a heterologous protein that is co-regulated with calprotectin, in the stool sample. Calprotectin elevated to about 50-120 µg per gram of stool indicates low-grade inflammation of the gastrointestinal tract; calprotectin elevated to more than about 120 µg per gram of stool indicates significant inflammation in the GI tract; and calprotectin elevated to more than about 250 µg per gram of stool indicates severe inflammation in the GI tract. Elevation to over about 250 µg/g also indicates that a patient with inflammatory bowel disease is at high risk of relapse within one year. Signs of inflammation can be analyzed further by assessing intestinal permeability, testing for food allergies, and/or performing a comprehensive parasitology profile.

The third test, to examine gut flora, includes testing for harmful and imbalanced gut flora and preferably includes testing for both harmful and non-harmful (e.g., non-pathogenic or beneficial) gut flora. Harmful gut flora includes, but is not limited to, *Clostridium difficile* and *Helicobactor pylori*; imbalanced gut flora includes, but is not limited to, *Klebsiella* species, *Pseudomonas* species, and *Clostridial* species; and beneficial gut flora includes, but is not limited to, *lactobacillus* species, *bifidobacteria* species, and *Escherichia coli*. Where there is a presence of harmful bacteria, an excess of imbalanced gut flora and/or insufficient beneficial gut flora, there is a maldistribution of flora within the total community. The presence of harmful bacteria, an excess of imbalanced flora and/or an insufficiency of beneficial gut flora are all forms of dysbiosis. Treatment for dysbiosis can include probiotic treatment, and when the gut contains harmful gut flora or imbalanced flora, a patient can also be treated with anti-microbial herbs and/or antibiotics.

Regardless of outcome, the methods of the invention or a step within the methods (e.g., testing for inflammation) can be repeated at a later point in time (e.g., six weeks later). Thus, the methods of the invention can be repeated periodically and used to monitor a patient. The monitoring can determine whether a treatment (e.g., a drug treatment) or lifestyle change (e.g., a change in diet or exercise) is having a measurable effect on the tested parameter(s).

In another aspect, the invention features kits that can be used to provide stool specimens in a condition suitable for testing in the manner described above. For example, a kit for the collection of a stool sample can include (a) a collection tub; (b) a tube containing a fixative medium; (c) a tube containing a medium that maintains the relative proportions of organisms in a stool sample; and (d) written materials. The fixative medium maintains the integrity of organisms within the stool for analysis, and a suitable example is SAF medium. The medium that maintains the organisms (i.e., a medium that does not selective kill or selectively support any given organism) can be Cary-Blair medium.

The written materials can be presented in various forms and can include one or more of: (a) instructions for use; (b) a requisition form; and (c) a mailing envelope or other materials for transporting the sample.

In addition to the components listed above, the kit can include other items such as one or more of: (a) a holder to suspend the collection tub over a toilet; (b) an empty cup; (c) an absorbent pad; (d) a flat tool suitable for insertion into a hand-held tube (e.g., a wooden stick such as a tongue depressor or a similarly shaped item made from wood, plastic, or other materials); and (e) a glove (e.g., a disposable glove, which may be biodegradable).

An IBS diagnosis is based on identifying positive symptoms consistent with the condition and excluding other conditions with similar clinical presentations. IBS symptoms often mimic those associated with other GI conditions, such as maldigestion and disorders of absorption (e.g., celiac disease, lactose intolerance, pancreatic insufficiency), infection and dysbiosis, as well as inflammatory bowel disease. IBS is differentiated from IBD (irritable bowel disease) in that, unlike IBD, IBS does not cause severe inflammation, ulcers or other damage to the bowel. Where the only diagnosis is a diagnosis of exclusion, the average time from the onset of symptoms to a positive diagnosis of IBS is nearly three years.

In addition, incorrect symptom attribution may lead to referral to a gastroenterologist and unnecessary procedures (such as colonoscopy or endoscopy), hospitalization, or surgery (e.g., appendectomy, cholecystectomy, or hysterectomy). Currently, Rome III criteria are used to diagnose functional gastrointestinal disorders such as IBS, although these criteria are not significantly utilized in primary care (as they do not differentiate therapeutic choices). Diagnosis based on tests to evaluate digestion, inflammation, and infection/gut microflora will result in more timely and accurate diagnosis of IBS.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 3 is a representative report illustrating the manner in which information obtained in the methods of the invention can be conveyed to a clinician. The report can be supplied physically or by computer graphics.

DETAILED DESCRIPTION

Figure 1:
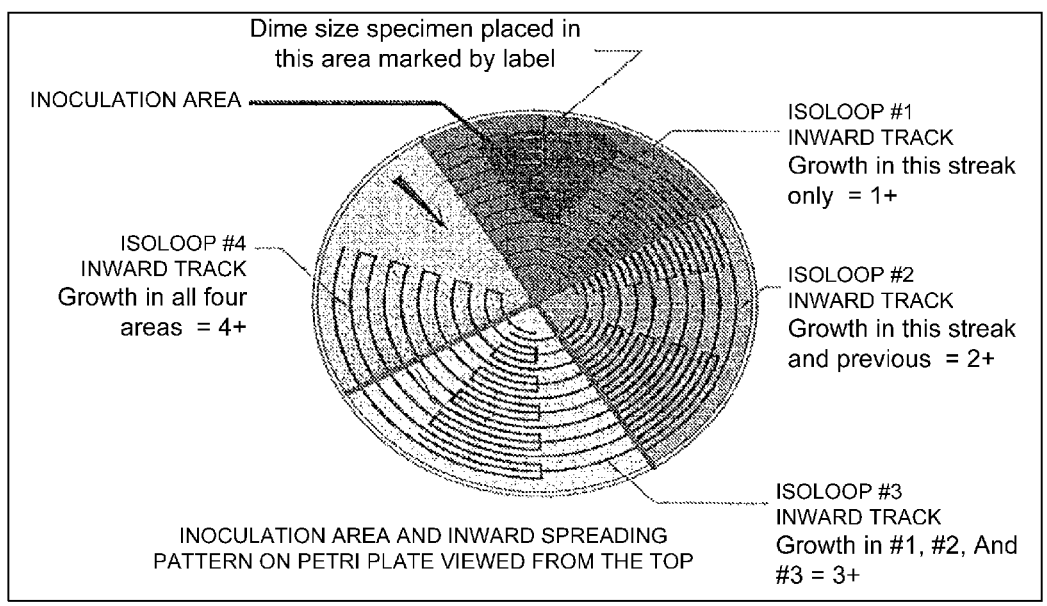
FIG. 1 is a schematic representation of a culture plate, divided into quadrants, that has been inoculated and streaked using the spreading pattern shown.
Figure 2:
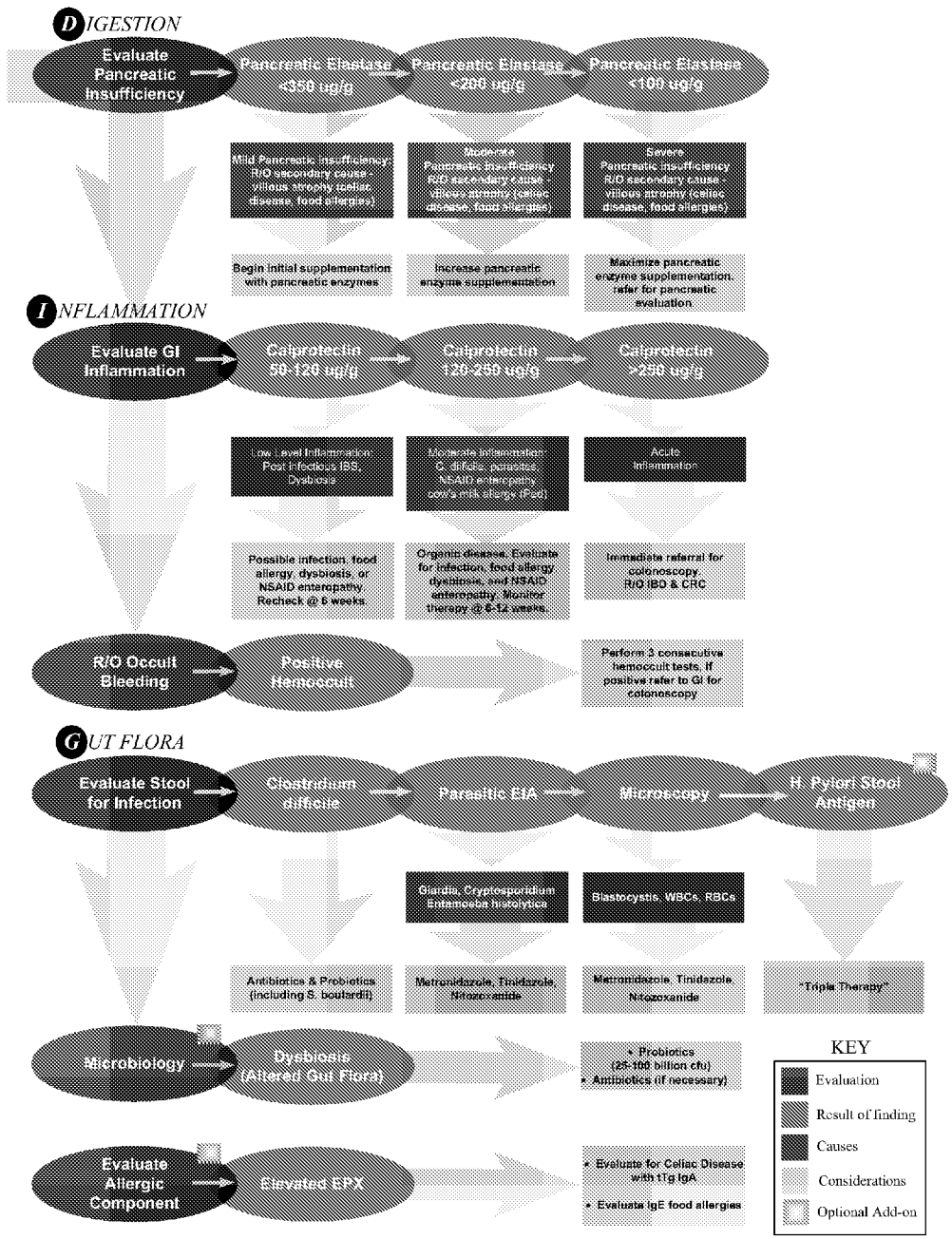
FIG. 2 is a flow chart depicting representative analytes and pathogens that can be assessed to evaluate digestion, inflammation, and gut flora in a patient.

The compositions and methods described herein can be used to assess gastrointestinal health in virtually any patient, regardless of age and regardless of whether or not the patient has any specific symptom or complaint (i.e., the method can be carried out on a patient in good health). In many cases, however, the patient will be a person who is complaining of abdominal pain, perhaps associated with gas or bloating, constipation or diarrhea, or other symptoms of a gastrointestinal disease or disorder.

Chronic maldigestion can lead to bacterial or fungal overgrowth and alterations in gut permeability. Toxins and large molecules that escape the intestinal barrier can enter the general circulation, inflame the liver, burden the body's detoxification system, and increase the risk for food allergies, joint disease, and imbalances in overall health. Malabsorption can lead to deficiencies of nutrients, proteins, carbohydrates and fats. This can result in long term health complications such as anemia, malnutrition, impaired metabolism and other diseases, such as osteoporosis. Chronic dysbiosis (a microbial imbalance) can lower the levels of beneficial short chain fatty acids and alter bacterial metabolic activity, thereby increasing the risk of carcinogenesis, hormonal imbalance, and GI inflammation. Altered GI immune function and exposure to bacterial pathogens can lead to diarrhea, mucosal inflammation, intestinal permeability, toxin production and autoimmune disorders. Although the invention is not so limited, patients suspected of suffering from one or more of these conditions (e.g., patients complaining of any of these symptoms or exhibiting signs of any of these conditions) are candidates for testing as described herein. Further, any of the methods described herein can include a step of identifying a patient as a candidate for testing (e.g., a patient complaining of gastrointestinal distress or exhibiting signs of an associated condition). For example, the methods can include a step of questioning a patient about their gastrointestinal health and/or performing a physical examination.

Digestion can be assessed by testing for pancreatic sufficiency or insufficiency, as the case may be, which can, in turn, be assessed by determining the level of expression or activity of a protein that is produced primarily or exclusively by the pancreas and that remains stable or detectable following passage through the intestine. For example, one can assess a pancreatic elastase (PE), for example PE1, or another marker of pancreatic function (e.g., a protein that is co-regulated with pancreatic elastase). Pancreatic elastases are produced by the human pancreas and, as noted, are an indicator of exocrine pancreatic function, as levels of PE are largely unaffected by transit through the GI tract or enzyme supplementation. These levels correlate with duodenal outputs of amylase, lipase, trypsin, and chymotrypsin, which may also be assessed. PE levels from 100-200 µg/g of stool are associated with moderate pancreatic insufficiency, whereas values below 100 µg/g indicate severe pancreatic insufficiency. Clinically, decreased levels of PE in stool reflect the need for exogenous digestive enzyme supplementation to support exocrine pancreatic deficiency.

Expression and activity of PE can be assessed in numerous ways using techniques known in the art. For example, PE expression can be detected with proteins that specifically bind PE (e.g., an anti-PE antibody). In a particular embodiment, PE expression can be assessed using a commercially available test, such as the ScheBo® PE1 kit (ScheBo Biotech, Giessen Germany). A random stool sample can be collected according to the patient instructions provided with the kit. Briefly, a 100 ml polypropylene container is filled ¼-¼ full with stool by the patient and homogenized using the tool (e.g., a wooden tongue depressor) provided. The container is closed tightly, placed in a shipping device, and sent to the laboratory. Stool samples should be received by the lab within 8 days of collection and are stable for three days thereafter when stored at 2-8° C. Frozen aliquots are set up in 1.5 ml microcentrifuge tubes for longer storage at −20° C. Of course, samples may be provided otherwise. For example, samples may be collected from hospitalized patients and taken directly to the hospital's lab or a nearby testing facility.

In the ScheBo® PE assay, an ELISA plate is coated with a monoclonal antibody that specifically binds human PE1. PE1 present in a sample or standard is bound to the antibody and thereby immobilized on the plate. A complex of monoclonal anti-PE1-biotin and peroxidase (POD)-streptavidin binds to PE during the next incubation. The peroxidase oxidizes ABTS (2,2'-azino-bis(3-ethylbenzothiazolin-6-sulfonic acid) diammonium salt), which turns dark green. Finally, the concentration of oxidized ABTS is determined photometrically. Polyclonal antibodies can also be used to detect proteins such as PE1 that are produced by the pancreas and stably transported through the gastrointestinal tract.

As noted, PE1 serves to indicate pancreatic function (e.g., sufficiency or insufficiency). Where levels are greater than about 200 µg/g of stool, exocrine pancreatic function is adequate and no further action is necessary with respect to pancreatic function. However, a physician may wish to consider pancreatic supplementation if levels are in the low normal range (e.g., 200-350 µg/g). Healthy individual produce more than 500 µg/g of PE. Thus, levels between about 200 and 500 µg/g suggest a deviation from optimal pancreatic function. Where this outcome is found, the clinician should consider digestive enzyme supplementation if one or more of the following conditions is present: loose, watery stools; undigested food in the stool; post-prandial abdominal pain; nausea or colicky abdominal pain; gastroesophageal reflux symptoms; bloating or food intolerance. Low levels of PE1 (for example, ~100-200 µg PE/g of stool) indicate mild to moderate pancreatic insufficiency and pancreatic enzyme supplementation as well as further testing to assess intestinal permeability and to determine the profile of intestinal parasites is advised. Celiac testing can also be performed. Very low levels of PE1 (for example, <~100 µg PE per gram of stool) indicate moderate to severe pancreatic insufficiency. In this event, pancreatic enzyme supplementation and vitamin and mineral supplementation are indicated.

In addition to treatments targeted to the pancreas, physicians may wish to consider other medical tests and treatments. For example, reduced PE is found in over 50% of type 1 diabetics and 35% of type 2 diabetics. Diabetes secondary to exocrine disease could be much more frequent than previously thought; studies have shown that low PE is closely related to glycemic control. Exocrine pancreatic function is also frequently impaired in gallstone sufferers and post-cholecystectomy patients. There is a high prevalence of pathological changes in exocrine pancreatic function in patients with gallstones. Nearly one third of patients with osteoporosis have reduced concentrations of PE. Vitamin D levels may also be significantly decreased in these patients. PE is also useful in monitoring exocrine pancreatic function caused by: chronic pancreatitis, auto-immunopathies and connective tissue diseases, chronic inflammatory bowel disease, and intestinal malabsorption with mucosal atrophy. A transient reduction of PE can occur with villous atrophy. After mucosal regeneration, PE levels return to normal. PE can therefore be used as a monitoring tool in patients with Celiac disease and other malabsorptive conditions. Accordingly, the present methods in which digestion is assessed by examining PE can be carried out periodically to monitor a patient's condition and/or recovery, and the methods can be expanded to include other tests such as those mentioned above. For example, further testing can include one or more of: bone resorption assessment, glucose/insulin analysis, Celiac testing, and testing for bacterial overgrowth in the small intestine.

Another way to assess digestion is by evaluating stool alpha 1 chymotrypsin levels or assessing fecal fat content. Chymotrypsin is an enzyme secreted by the pancreas that functions in protein digestion. Levels of stool chymotrypsin can be determined using a stool sample that is collected as described herein and preserved in a minimal microbial growth media. A high salt surfactant can be used to release the chymotrypsin contained within the sample. The reaction of the free chymotrypsin with a spectrophotometrically active substrate facilitates the determination of chymotrypsin activity in the sample. Results can be expressed as units of chymotryptic activity relative to the grams of stool analyzed. A normal result for this assay is ~0.9-26.8 U/g stool. Low levels of chymotrypsin (<0.9 U/g) indicate exocrine pancreatic insufficiency. Therapy should include exogenous supplementation of pancreatic enzymes including lipase. Elevated levels of chymotrypsin (>26.8 U/g) suggest a rapid transit time (diarrhea). A faster transit time reduces the intestinal degradation of chymotrypsin, which results in an increased recovery of this enzyme. Chymotrypsin could also be elevated with excess pancreatic enzyme supplementation.

As both pancreatic elastase and chymotrypsin are indicators of exocrine pancreatic function, the clinical indications for PE also apply to cymotrypsin. Therefore, the methods in which chymotrypsin is assessed can also include a step of identifying a patient who has: loose, watery stools, undigested food in the stool, post-prandial abdominal pain, nausea or colicky abdominal pain, gastroesophageal reflux symptoms, or bloating or food intolerance. Other conditions associated with reduced chymotrypsin include diabetes, cystic fibrosis, chronic pancreatitis, and malabsorption.

Both chymotrypsin and PE are highly accurate in distinguishing between pancreatic maldigestion and intestinal malabsorption (82% and 92%, respectively). PE is not affected by bovine or porcine enzyme supplements, so patients do not have to discontinue therapy to assess baseline levels. Chymotrypsin is affected by exogenous supplementation, which makes it an ideal tool to monitor dosing adequacy. When chymotrypsin values fall within the reference range in supplemented individuals, the clinician can be confident that an appropriate dosage of digestive enzymes is being administered. As noted, the present methods can be carried out not only in the context of an initial presentation and diagnosis, but also in the context of ongoing monitoring. While PE may be a more accurate non-invasive marker to assess exocrine pancreatic function, chymotrypsin is the preferred marker to monitor enzyme supplementation.

Elevated levels of fecal fat (e.g., elevated cumulative levels) are also an indicator of maldigestion. Fecal fats include triglycerides, long chain fatty acids (LCFAs), cholesterol and phospholipids, which can be extracted with methods known in the art and measured individually to obtain a measure of fecal fat levels. To evaluate fecal fat, a stool sample can be submitted in a preservative (e.g., 5% formalin), and lipids can be extracted from the sample using an organic extraction. Once the stool lipids are isolated, standard automated chemistry assays can be used to determine the levels of the individual fecal fat components, including triglycerides, cholesterol, phospholipids and long chain fatty acids. Cumulative totals of these components outside the range of 2.6 to 332.4 mg/g stool are indicative of malabsorption Triglycerides represent the major component of dietary fat (on average 120 g of a 125 g daily load). Elevated levels are suggestive of incomplete fat hydrolysis, which can be caused by exocrine pancreatic insufficiency or bile acid insufficiency. Elevated triglycerides with normal LCFAs have been noted in patients with steatorrhea due to pancreatic insufficiency. Triglycerides may also be elevated with rapid transit time, which impairs the breakdown and absorption of these lipids.

LCFAs are normally readily absorbed in a healthy mucosa. Elevated levels suggest malabsorption, reduced pancreatic function or bile insufficiency. Increased LCFAs have also been noted after acute intestinal infections.

Fecal cholesterol is derived from the diet, bile, and from mucosal epithelial break-down. In a healthy gastrointestinal tract, about 40-60% of dietary cholesterol will be absorbed. Elevated levels are a reflection of mucosal malabsorption. Impaired absorption of fecal cholesterol occurs in Celiac disease secondary to damaged mucosa from gluten ingestion.

Phospholipids are derived from three specific sources: bile (50%), diet (25%), and mucosal desquamation (25%). The major dietary-derived phospholipids include phosphatidyl choline, phosphatidyl serine, phosphatidyl ethanolamine and cardiolipin. In a healthy individual, nearly 85% of intestinal phsopholipids are absorbed. As phospholipids are derived from more than one source, elevations could occur from the following: malabsorption, inadequate bile salt resorption, or increased mucosal cell turnover. Referring to other absorptive markers can help determine the cause of high fecal phospholipids.

The following conditions can contribute to the impaired absorption of fecal fat: pancreatic insufficiency (specifically lipase), cholestasis (e.g., biliary obstruction or liver disease), interrupted enterohepatic circulation (e.g., ileal disease or bile salt deconjugation from small bowel bacterial overgrowth), Celiac disease, short bowel syndrome, and Whipple's disease (rare). In general, an elevation in any one of the fecal fat markers is suggestive of malabsorption (see above for the clinical significance of individual absorptive markers).

Inflammation affecting the GI tract can be detected in a variety of ways, including by tests for calprotectin expression and occult blood. Calprotectin is a calcium-binding protein found primarily in neutrophils that serves as a direct marker of intestinal inflammation. Infection, tissue damage, or increased permeability of the mucosa results in the migration of granulocytes into the intestinal lumen. As with PE, calprotectin can be detected by methods known in the art, including methods in which a calprotectin-specific binder is used to detect expression. For example, one can use the PhiCal® quantitative EIA (Calpro AS).

Calprotectin is a useful analyte because it is resistant to bacterial degradation in the gut and is stable in stool for up to one week at room temperature. It is also unaffected by medications, dietary supplements, and enzymatic degradation. Further, calprotectin: reflects the flux of leukocytes into the intestinal lumen; is released upon activation and degranulation of neutrophils; correlates strongly with 111-indium-labeled leukocyte excretion as well as histologic and endoscopic grading of disease activity in ulcerative colitis; helps differentiate between IBS and active IBD; predicts relapse in patients with IBD and serves as an objective marker to assist in treatment protocols; and assists in selecting patients for endoscopy and in monitoring responses to treatment (especially in children who may require general anesthesia to undergo more invasive analyses).

For calprotectin analysis, a random stool sample is collected according to patient instructions for the calprotectin PhiCal® test. Briefly, a suitable container (e.g., a 100 ml polypropylene tube) is filled ¼-⅓ full with stool by the patient and homogenized using a tool, such as a wooden tongue depressor. Controls for low and high calprotectin expression can be assayed with each batch of samples. PhiCal® uses a polyclonal antibody against calprotectin that is absorbed to the surface of a plastic well to bind calprotectin in diluted stool samples. As the antibody is linked to an enzyme, a subsequent reaction in which the enzyme catalyzes a reaction to yield a detectable (e.g., fluorescent or colored) product provides an easy means for detecting and quantitating bound calprotectin. Values below ~50 µg of calprotectin per gram of stool are not indicative of inflammation in the GI tract, and no further action is necessary based on this result. Values between 50-120 µg/g stool are associated with low-grade inflammation, which could be due to post-infectious irritable bowel syndrome (IBS), infection, food allergies, polyps, neoplasia, non-steroidal anti-inflammatory drugs (NSAIDs) or IBD in remission. It is prudent in these cases to repeat the calprotectin assay after about six weeks. If levels remain elevated after ruling out other etiologies, further investigative tests (e.g., endoscopy or imaging) should be considered. These further tests include: stool culture, an intestinal permeability assessment, a food antibody assessment, and a comprehensive parasitology profile. Therapeutic intevention includes probiotics, fish oils, N-acetylglucosamine, and/or rutin. Calprotectin expression above ~120 µg/g indicates significant inflammation, possibly caused by IBD, infection, food allergies, NSAID use, polyps, adenomas, colorectal cancer, or diverticulitis. Unless the source of the inflammation is clear, further evaluation is recommended and may include endoscopy and/or colonoscopy. One can also assess microbiology/parasitology at this stage, and further testing includes any of the tests listed above in connection with lower elevation of calprotectin. Where calprotectin is severely elevated (>250 µg/g), there is a strong likelihood that the patient has active IBD or are at a high risk of relapse to active IBD within one year. In this event, IBD should be managed with standard therapies. Intervention can include administration of probiotics, fish oils, N-acetylglucosamine, rutin, and/or anti-inflammatory agents (e.g., leukotriene inhibitors and TNF-alpha antagonists). For patients with IBD, calprotectin levels between 250-500 µg/g indicate low to moderate disease activity. Levels above 500 µg/g suggest high disease activity. Patients with IBD in remission and levels above 250 µg/g have a high risk of relapse within one year.

Where calprotectin levels are above 120 µg/g, there is likely significant inflammation in the gastrointestinal tract. The cause could be IBD, infection, NSAID use, polyps, adenomas, or colorectal cancer. Calprotectin may also be elevated in children with chronic diarrhea secondary to cow's milk allergy or multiple food allergies. Further procedures can be carried out to determine the cause more specifically. Levels ranging from 50-120 µg/g indicate less severe inflammation. Values below 50 µg/g indicate there is little or no inflammation in the gastrointestinal tract.

Regardless of the cause, patients with elevated calprotectin should be tested further with, for example, an intestinal permeability assessment, an allergy antibody assessment, Celiac panel, ImmunoGenomic™ profile, or a comprehensive parasitology profile.

Another marker for inflammation is an eosinophil protein (e.g., eosinophil protein X or EPX, also known as eosinophil-derived neurotoxin (EDN)). In healthy individuals, eosinophils reside in the connective tissue layer of the gut, known as the lamina propria. It is not until damage occurs to the lamina propria that eosinophils migrate into the gut lumen. Eosinophils contain a number of highly cationic proteins such as eosinophil cationic protein, major basic protein, eosinophil peroxidase, and EPX. Upon eosinophil degranulation, these cationic proteins are release and can be assayed. As the proteins possess cytotoxic proerties, their accumulation is associated with inflammation and tissue damage.

While assessing eosinophilic activity is informative, tests that require colonoscopy or biopsy have limited utility for office-based practitioners. Eosinophil markers in stool, however, can be assayed according to the present methods as indicators of inflammation. As with other markers described herein, eosinophilic markers can provide information regarding a patient's initial treatment and can be assayed over time to monitor that treatment. For example, baseline levels of EPX can be used to determine intestinal inflammation associated with food allergy and to monitor dietary changes. Studies have demonstrated a significant reduction in EPX after three months on a successful elimination diet.

Assays for EPX can be based on extraction of EPX from neat stool using a cationic extraction buffer. Once extracted, the protein can be detected and quantitated using any EPX-specific binding protein (e.g., an antibody). Eosinophils are bone-marrow derived cells that secrete a range of highly toxic granule proteins and other inflammatory mediators. The cells are characterized by the presence of dense granular deposits in their cytoplasm that contain proteins that mediate the inflammatory response and tissue damage. EPX is one of the highly cationic proteins contained within these granules. Eosinophils play a role in allergy and in the response to parasites and are found in significant numbers in the underlying connective tissue of the respiratory, gastrointestinal, and urogenital tracts. Biopsies of patients with IBD (ulcerative colitis and Crohn's disease) or Celiac disease have demonstrated marked infiltration of eosinophils. This infiltration plays a role in the pathogenesis of the inflammatory processes associated with these disease states. Further, increased levels of EPX have been demonstrated in the feces of patients with active disease.

If desired, EPX can be evaluated using the EDN kit available from the Medical and Biological Laboratories Co., Ltd (MBL). Once extracted, EDX is quantified using a sandwich ELISA. The reportable range of the assay is 0.9 ng/ml to 40.0 ng/ml. Where EPX is present at <~7.0 µg/g, there is no active inflammation of the GI tract. However, elevated levels of EPX (>~7.0 µg/g) indicate inflammation and/or tissue damage in the GI tract. Underlying causes include food allergy and/or atopic dermatitis, protein-sensitive enteropathy, helminthic infection, IBD, allergic colitis, chronic diarrhea, chronic alcoholism, bowel cancer, eosinophilic gasteroenteritis (rare), and gastroesophageal reflux. Increased levels of EPX have also been found in ulcerative colitis and Crohn's Disease, with elevations correlating with disease activity. As a non-invasive marker, EPX offers increased sensitivity for evaluating inflammatory disease activity and for predicting relapses in patients with IBD.

Occult blood is blood in the stool that is present in amounts too small to be seen but large enough to be detected by chemical tests. In our methods, we test for occult blood as an indicator of inflammation and a sign of certain gastrointestinal disorders. Occult blood can be detected in several ways, including by immunoassays for hemoglobin. For convenience, one can use a commercially available test such as the Hemosure® One Step Immunological Fecal Occult Blood (iFOB) test supplied by Quidel Corporation. This test is a rapid, qualitative, sandwich dye conjugate immunoassay for the detection of human hemoglobin in feces. It employs a unique combination of monoclonal and polyclonal antibodies to selectively identify hemoglobin in test samples with a high degree of sensitivity. In less than five minutes, elevated levels of human hemoglobin as low as 0.05 µg hHb/ml can be detected and positive results for high levels of hemoglobin can be seen in the test as early as two to three minutes. Stool samples in Cary-Blair medium can be tested in this assay within about seven days, and stools collected in the preservation buffer tube are stable as follows: for six days at 37° C., six months at 4° C., and 20 months at −20° C. A monoclonal antibody-based assay that can be used is the Hemosure® test, which is specific for human hemoglobin.

A positive result can indicate ulcers (e.g., peptic ulcers), polyps, diverticulitis, IBD, or colorectal cancer. Bowel lesions, polyps and colorectal cancers may not bleed or may bleed intermittently, however, and a test result can be negative even when disease is present for this reason. Repeated testing is advisable if symptoms persist, and physicians are likely to order repeated testing for occult blood as well as other, invasive tests (e.g., colonoscopy) or imaging (e.g., a barium enema) whenever colorectal cancer is suspected. Patients should be cautioned not to take vitamin C supplements for several days prior to testing for occult blood, as ingestion over about 250 mg of vitamin C per day inactivates the test.

Conversely, a test can be positive in healthy patients because certain medications may cause gastrointestinal irritation resulting in occult bleeding. These include rectal suppositories and oral medications such as aspirin and corticosteroids. If a patient has not refrained from eating undercooked meats, a false positive result may ensue. However, the Hemosure® iFOB test is highly specific and should not react to hemoglobin from fish, beef, chicken, rabbit, or goat. Stool samples may also become contaminated with blood if collected during menstrual bleeding or if a patient has blood in the urine. Positive and negative controls should be run with each test. The positive control can be diluted human blood, and the negative control can be a known blood-free sample, such as water or a buffered solution.

Accordingly, the present methods can include repeated occult blood tests, positive and negative controls for occult blood, and a step of obtaining information from a patient regarding vitamin C intake, meat intake, and menstruation.

Where the present methods assess inflammation, they can also include an assay for lactoferrin. Human lactoferrin is an 80 kilodalton glycoprotein that binds iron and is secreted by most mucosal membranes. It is a major component of polymorphonuclear neutrophils (PMNs), which are the primary component of an acute inflammatory response.

Assessing inflammation is especially useful in distinguishing IBS from IBD, as there is little if any inflammation associated with the former condition.

Lactoferrin can be assessed in a number of ways, including the IBD-Chek™ test, which uses antibodies to human lactoferrin. The microtiter wells contain immobilized polyclonal antibody against lactoferin. The detecting antibody consists of polyclonal antibody conjugated to horseradish peroxidase. In the assay an aliquot of fecal specimen is emulsified in the diluent and transferred to a microtiter well. Any lactoferrin present in the sample binds to the immobilized antibody. After incubation, the wells are washed and the conjugated antibody is added. A second wash step removes unbound conjugate. With the addition of substrate, any conjugate present as the result of bound lactoferrin results in color formation, which can be quatitated with a spectrophotometer. At 450/620 nm, a negative result is <0.160, a positive result is ≥0.160. All positive results should be confirmed by repeat testing.

In the paragraphs that follow, we discuss methods for assessing gut flora.

Identification of microorganisms is key to determining microbial imbalance due to redistributions within the microbiome, parasitic infections, and other changes in gut flora. Traditional culture methods enable the identification and semi-quantitation of specific organisms through the utilization of differential growth media. This can also be accomplished using automated biochemical instruments such as Vitek. Other methods and techniques that can be used include mass spectrometry methods such as MALDI-TOF-MS (Matrix-assisted laser desorption/ionization time-of-flight mass spectrometry). The methodology uses species- and strain-specific biomarkers to identify organisms. Microarray technology can also be used to evaluate nucleic acids such as 16sRNA, small peptides or molecules such as toxins that are specific for the microorganism, Carbohydrate (e.g., polysaccharide) profiles can also be determined. Nucleic acid probe technology can also be used in combination with fluorescent microscopy for microbial quantification and identification. Other methods for assessing the microbiome include nucleic acid amplification by PCR and RNA or DNA sequencing.

General Stool Culture Procedure:

Methods suitable for use in culturing or otherwise treating stool samples are known in the art and can be used in the context of the present invention. In the following paragraphs, we provide information regarding the processing, testing, and interpretation of stool bacterial cultures. These processes can be used to generally evaluate the microbial community rather than to diagnose infectious disease by analyzing pure cultures of specific organisms.

The microbial community that resides in the gastrointestinal tract is comprised of numerous species of naturally occurring bacteria. While some defined organisms are clearly harmful, most bacteria that typically found in the GI tract are beneficial and are present in numbers that promote good health. More specifically, beneficial bacteria, such as lactobacilli and bifidobacteria, play an important role in promoting a healthy gut microflora environment and ensuring proper digestion. These organisms can prevent the over-colonization of the gut with pathogenic organisms and may reduce the risk of certain gastrointestinal diseases. The role of some commensal organisms may vary depending on their presence as a percentage of the total bacterial population. Using the present methods, one can evaluate the bacteria present in a stool sample in a more comprehensive way. Identifying each organism and enumerating it relative to other isolates provides the clinician with a picture of the microbial community present in the GI tract and, more specifically, the colonic environment, at the time the sample was collected. This information is useful in determining whether the patient is suffering from clinical gastritis or subtle, atypical aberrations that may indicate a sub-clinical disease process. The bacteria present can be categorized as harmful (or pathogenic), potentially harmful (or pathogenic), or beneficial.

Several factors may affect the composition of the colonic flora, including diet, transit time, stool pH, age, microbial interactions, colonic availability of nutrients, bile acids, and sulfate, as well as the ability of the microbes to metabolize these substrates.

The predominant beneficial flora in the large intestine are the bifidobacteria, which constitute as much as 25% of the overall colonic flora in healthy adults. Recovery of these organisms from the colon should therefore ideally be in the 3+ or 4+ ranges. In the colon, obligate anaerobes such as bifidobacteria predominate over facultative anaerobes such as lactobacilli by 1000:1. It is for this reason that lactobacilli growth as low as 1+ or 2+ is considered normal in healthy adults. Non-pathogenic *E. coli* populate the distal colon, although they are usually found in reduced quantities, comparable to levels of lactobacilli. A 1+ to 2+ concentration of non-pathogenic *E. coli* is therefore considered normal.

Organisms of the genera *Salmonella*, *Campylobacter*, and *Shigella* have been associated with the production of a broad spectrum of clinical symptoms observed in the event of bacterial gastritis. Accordingly, these organisms are designated as pathogens and their presence normally results in acute diarrhea. Other traditionally recognized intestinal pathogens include enterotoxigenic *E. coli*, *Shigella*, *Yersinia*, *Pleisiomonas*, *Vibrios*, *Aeromonas*, *Campylobacter*, the viral pathogen rotavirus, and the parasites *Cryptosporidium* and *Coccidia*. A number of other bacteria have been associated with gastrointestinal discomfort, but their etiologic role is still largely undetermined.

Organisms such as *Citrobacter freundii*, *Enterobacter cloacae*, and *Klebsiella pneumoniae* are usually classified as "normal" flora. However, some studies have associated these and other organisms with various gastrointestinal complaints when they are the predominant organisms identified on stool culture in the absence of other frank pathogens. The presence of traditionally non-pathogenic bacteria in predominating numbers could indicate a dysbiotic state in the colon. These organisms may be the direct cause of a gastrointestinal disturbance, they may be aggravating such a disturbance, or they may simply be present as an indicator of some other disruptive process. Accordingly, we tend to classify these organisms as potential pathogens. Yeast have also been associated with clinical syndromes related to dysbiotic colonic environments. There are no definitively recognized pathogenic yeast, and we therefore refer to yeast as a potential pathogen when present in elevated numbers. *Candida albicans* is the most significant isolate of yeast, and its presence is associated with a broad spectrum of clinical conditions.

Beneficial bacteria are organisms whose presence in substantial numbers has been associated with a healthy colonic environment. These bacteria include *Bifidobacterium* sp., *Lactobacillus* sp. and *Escherichia coli*.

Useful materials include: stool transport (Cary-Blair media); blood agar plates; Maconkey agar plates; colistin-nalidixic acid (CNA) plates; hektoen-enteric agar (HE) plates; oxyrase bidifobacter agar plates; *candida* ID agar plates; sterile swabs; gloves; isoplater instrument (for automated streaking); and an incubator.

Samples arriving for testing may be in a transport media that preserves stool bacteria. Preferably, the transport media suspends active metabolism but preserves viability. A suitable medium is the Cary-Blair formula manufactured by the MML company. Samples preserved in this medium can be reliably tested up to six days after they have been collected from a patient.

To inoculate plates, the sample can be mixed before using a sterile swab to transfer a sample of stool onto the surface of a culture plate (e.g., to about a 0.5×0.5 cm patch). To assess bacteria, one can inoculate one or more plates holding the following culture media: blood agar (BAP), Hektoen-enteric agar, Maconkey (MAC) agar, colistin-nalidix acid (CNA), *candida* ID agar, and MCA bifidobacter agar. The sample can then be further distributed on the surface of the agar either manually (e.g. using a sterile loop or needle) or by an automated streaker instrument. Typically, the MCA bifidobacter agar and the *candida* ID agar are manually streaked. The plates are then incubated (e.g., at 30-37° C.) for a number of hours (e.g., 8-24 hours or more) prior to evaluation. Some plates (e.g., the bifidobacter agar plates can be incubated longer (e.g., at 35° C. for at least or about 72 hours). *Candida* ID agar plates can be incubated for at least or about 72 hours at 35° C.

Following incubation, the plates can be assessed in numerous ways. For example, one can begin by noting changes in morphology. The CNA plate can be evaluated for alpha-hemolysis (green), gamma-hemolysis (no hemolysis) and/or beta-hemolysis (clearing of agar immediately surrounding a colony). Isolates can be recovered from this plate and others. *Lactobacillus*, *Streptococcus*, and *Staphylococcus* are a few of the isolates that may be recovered from this plate. The HE agar plate can be examined for the presence of lactose (yellow) and non-lactose fermenters, hydrogen sulfide producers (black pigment) and clearly mucoid colonies. These plates are useful in isolating *Salmonella*, which produce hydrogen sulfide, and *Shigella*, which do not ferment lactose and appear as clear colonies. Maconkey agar can be used to identify gram-negative organisms. Almost all enteric bacilli will grow on this media. Lactose fermenting colonies (pink), non-lactose fermenting colonies (grayish or colorless), and mucoid colonies may appear on these plates. The blood agar plate can be compared to the other media. Swarming or beta-hemolysis that is present here but not on other plates should be pursued.

In addition to gross observations regarding morphology, one can identify and quantitate each organism. Growth quantitation is important for determining the significance of the organism. Referring to FIG. 1, organisms can be categorized according to the extent of their growth. For example, organisms growing in the first quadrant only can be designated "1+". Growth in the first and second quadrants would be categorized as "2+", and so forth. These determinations may be somewhat subjective. For example, if organisms on the plate are clearly isolated, and there is one discernable colony in quadrant 1 and 1 discernable colony in quadrant 2, the quantitative report could be very few colonies or 1+ growth.

However, if the reader is unable to determine the amount present in quadrant 1 (due, for example, to heavy growth of additional organisms), the outcome may be 2+ instead.

Affirmative identification of an organism can be carried out in several ways. Procedures for many different biochemical and media-based differential tests are known in the art. It is generally true that, regardless which test is used, the most accurate identifications are made when working with a pure culture. Thus, we stress the advantages of working on a single, well-isolated colony.

After quantifying and identifying the pathogens, one can assess minimum inhibitory concentrations or perform botanical assays. When indicated (e.g., when requested by a patient's physician), sensitivities and botanical assays can be performed on significant gram-negative enteric and non-enteric isolates (e.g., *Staphylococcus aureus*, species of *bacillus*, and yeast isolates.

In any of the present methods, the original sample can be aliquoted, and portions can be subjected to ancillary testing.

Identifying Bacteria:

Any method known in the art can be used to identify a given bacterium in stool samples. For example, the present methods can include a step of identifying *Clostridium difficile*, and this may be done through identification of a toxin produced by these organisms. *C. difficile* is a gram-positive, anaerobic, spore-forming *bacillus* that is the most commonly identified cause of antibiotic-associated diarrheal disease. When broad-spectrum antibiotic use suppresses the normal intestinal flora, selective pressure allows toxigenic strains of *C. difficile* to multiply. The toxins produced by toxigenic *C. difficile* strains, toxin A and toxin B, have enterotoxic and cytotoxic effects, respectively. Disease may vary from mild diarrhea to a condition known as pseudomembranous colitis (PMC), which can be fatal if not treated.

*C. difficile* organisms may not cause symptoms in 2-3% of healthy adults, 20-30% of hospitalized patients, and 50% of children under two years old. Thus, culture alone may be inadequate to document *C. difficile* disease.

*C. difficile* antigens, including toxin A and toxin B, can be detected with specific binding proteins (e.g., antibodies). Commercially available assays, such as the ProSpecT® *Clostridium difficile* Toxin A/B Microplate Assay, can be used for convenience.

Other intestinal bacteria that can be assessed include *Helicobacter pylori*, which may be of particular note due to its association with gastritis, gastric ulcers, and stomach cancer. Virulence factors include a vacuole-promoting cytotoxin and a potent urease enzyme, which creates an alkaline microenvironment that may allow continued growth despite stomach acidity. Typically, infected hosts mount an inflammatory response that accounts for much of the tissue damage. This organism can be harbored in a "colonized" state in which no symptoms of gastric disease are present.

*H. pylori* is a small, curved, gram-negative *bacillus*. It is oxidase, urease, and catalase positive. It is slow-growing on culture and requires specific conditions for growth. These features can be exploited in testing for the presence of *H. pylori* in a sample. Identification can also be made through urea-breath testing, serological tests, and with gastric biopsy tissue. Commercially available kits for detecting *H. pylori* include the Premier Platinum HpSA enzyme immunoassay. This is a qualitative assay for detecting *H. pylori* antigens in human stool. It employs a plurality of monoclonal anti-*H. pylori* capture antibodies adsorbed onto microwells. Diluted patient samples and a peroxidase-conjugated antibody are added to the wells, and any unbound conjugated antibody is subsequently washed off. Enzyme substrate is added to produce a colored reaction product that can be detected visually or spectrophotometrically.

Identification of Protozoa:

To assess altered gut flora, one can also test stool samples for protozoa. For example, fecal slides (e.g., stained fecal slides) can be used to identify intestinal protozoan cysts, ova, and trophozoites. Slide-based procedures are advantageous in that the slides are semi-permanent; they can be preserved for re-inspection and can be shipped (e.g., to experts for consultation). While protozoa can also be detected by direct smear and concentration techniques, slide preparations are generally considered to be more reliable for detecting protozoa. For example, the slides can be prepared so they include areas of both thinner and thicker stool density, which is optimal for recovery and detection of parasites.

Stool samples can be prepared in several ways. While single samples can be tested, it may be preferable to test multiple samples (e.g., 2-4 samples) that were collected on different days or to pool multiple samples from the same patient (e.g., three samples collected over the course of about one week). The samples can be stored in SAF preservation medium (sodium acetate, 10% formalin), homogenized (e.g., by vortexing) and aliquotted. One or more aliquots can then be filtered and concentrated by centrifugation. The supernatant is discarded, and the resulting sediment is analyzed. Samples placed in SAF medium should be stable for about 60 days at room temperature.

By way of illustration, multiple stool samples from a single patient can be concentrated by: (1) removing the caps from each patient sample; (2) pouring an aliquot from each of the patient's sample vials into a clean, appropriately labeled, empty vial and mixing thoroughly; (3) capping the single vial including the mixed samples; (4) suspending the sample; (5) centrifuging the sample; (6) discarding the supernatant; and (7) reconstituting the pelleted sample. This procedure can be carried out using SpinCon® tubes (Meridian Diagnostics, Inc.) and Para-Pak Ultra® caps (Meridian Diagnostics, Inc.). In that event, the procedure can be carried out by: (1) removing the caps from each patient sample; (2) pouring an aliquot from each of the patient's sample vials into a clean, appropriately labeled, empty vial and mixing thoroughly; (3) capping the single vial including the mixed samples with a Para-Pak Ultra® filtration cap, removing the outer cap with the key provided, and breaking off the tab located inside the cap; (4) placing a SpinCon® tube onto the Para-Pak Ultra® cap, inverting and tapping the tube gently on the counter to allow approximately 3-5 ml of specimen to filter through the cap into the SpinCon® tube; (5) removing the SpinCon® tube from the cap and placing a plug cap on the tube; (6) centrifuging the tube (e.g., at about 500×g for 10 minutes); (7) removing the tub from the centrifuge and removing the top half of the tube; (8) removing half of the supernatant with a disposable plastic pipette from the bottom half of the SpinCon® tube and placing it in a 13×75 mm, appropriately labeled tube for EIA procedures; (9) reconstituting the sample by vortexing and pouring roughly half of the reconstituted sample into a clear polystyrene tube; and (10) recapping the bottom half of the SpinCon® tube and capping with a fresh plug cap. See also, Ash and Orihel, "Parasites: a guide to laboratory procedures and identification", ASCP Press 45-7-013-00 ISBN: 0-89189-231-1, 1987; Yang and Scholten, *Am. J. Clin. Path.* 67:300-304, 1977; and Meridian Diagnostics, Inc., package inserts for SpinCon and Para-Pak Ultra filtration devices, Rev. February 2001.

A suspension of a concentrated stool sample can be applied to a standard microscope slide along with Lugol's (5%)

iodine as a contrast agent. Parasite ova and cysts are detected microscopically and identified by morphology (e.g., shape, size, number of nuclei, cell structure, and other morphological attributes). PVA-preserved specimens are not recommended for iodine-stained preparations, but concentrated SAF or formalin-preserved stool can be used.

By way of illustration, one can prepare a slide by: (1) inserting a pipette into the tube or other vessel containing a stool sample and mixing; (2) removing a sample with the pipette and placing about one drop onto a plain microscope slide; (3) adding about one drop of iodine solution to the drop of sample; (4) mixing the iodine and stool sample with the corner of a glass coverslip; and (5) placing a coverslip over the sample. The preparation should be reasonably transparent. If it is too thick, it can be diluted with saline before the coverslip is placed. By microscopic examination, one can detect helminthes, ova, or larvae, and amoeba. Artifacts such as white blood cells and red blood cells may also be noted.

*Giardia* cysts are typically 8-19 μm in diameter. *Enterobacter* (e.g., *E. coli*) cysts have eight or more nuclei and are 15-25 μm in diameter. *Chilomastix* cysts are lemon-shaped, uni-nucleate, and 6-10 μm in diameter.

For trichrome slide preparation, samples can be concentrated (e.g., by the process described above) and prepared for staining by making a 1:1 dilution of the reconstituted sample and PVA in a tube (e.g., a polystyrene tube). The sample is then poured from the tube onto a paper towel, which absorbs the PVA but not the sample. The sample can then be transferred to a microscope slide using an applicator. Moving the applicator in a back-and-forth motion while rolling allows for a varied distribution of material on the slide, including thicker and thinner areas for examination. After transfer to the slide, the sample can be left to dry at room temperature.

Batches of samples prepared for trichrome staining and examination can be run with positive and negative controls. For example, two control slides can be stained with each batch of patient specimens; a negative control slide can be made from a sample known to be free of parasitic organisms and a positive control slide can be made from a sample known to contain protozoan cysts and trophozoites.

Trichrome staining is a rapid staining procedure that provides excellent differentiation of internal structures of intestinal parasites and separation of the organisms from background material. It is also rapid, easy, and suitable for fecal smears. The stain itself is the Wheatley modification of Gomori's trichrome stain for tissue sections, and it is highly stable. With well-fixed fecal smears, the staining characteristics of organisms are reasonably consistent, and the color contrast between organisms and background material render the organisms more easily visible than in hematoxalin-stained smears. The cytoplasm of organisms will usually stain a blue-green to purple, whereas nuclear chromatin, chromatoid bodies and other inclusions will stain red to reddish purple.

Suitable specimens include human stool samples in SAF preservative that have been concentrated with PVA added. The sample can be applied to labeled microscope slides and allowed to air dry (as described above). By way of illustration, we provide the following protocol, which can be carried out with a Jung Autostainer® instrument. The reagents required include alcohol (70% and 95%), acid alcohol (90%), and iodine alcohol (70%). Once the Jung Autostainer® has been turned on and self-initializes, it is ready to be loaded with the reagents and slides. The staining proceeds automatically as follows: (1) 70% iodine alcohol for 5 minutes; (2) 70% alcohol for 2-3 minutes; (3) 70% alcohol for 2-3 minutes; (4) trichrome stain for 10 minutes; (5) 90% acid alcohol dip; (6) 95% alcohol dip; (7) 95% alcohol dip; (8) 95% alcohol for five minutes; (9) 95% alcohol for five minutes; (10) 95% alcohol for five minutes; and (11) hemo-de solution for 25 minutes. The slides should not be allowed to dry out before a coverslip is applied. The coverslip can be a liquid coverslip such as Flo-Texx®.

In connection with these preparatory and staining methods, one can also consult: American Society of Clinical Pathologists, Laboratory Diagnostics of Intestinal Parasite Infection, CDC training course material; Wheatley, *Am. J. Clin. Pathol.* 21:330-991; Ash and Orihel, supra; NCCLS, Procedures for the Recovery and Identification of Parasites from the Intestinal Tract. M28-A Vol. 17 No. 23, 1997; and Jung Autostainer® Instruction Manual.

Upon inspection under the microscope, the cytoplasm of protozoan trophozoites should be a blue-green color and may be tinged with purple. Cysts tend to be more purple. Nuclei and inclusions (chromatoid bars, RBCs, and bacteria) and Charcot-Leyden crystals have a red color and are sometimes tinged with purple. Glycogen is dissolved by the fixatives and appears as a clear area in the organism. The background material usually stains green, which provides strong contrast with the protozoa. As noted, the contrast is often sharper than that observed with hematoxylin staining. Helminth ova, *Balantidium coli, Entamoeba coli* cysts and *Isospora belli* oocysts are best seen in wet preps, and acid-fast stains are recommended for *Cryptosporidium*.

The protozoa, host cells, yeast cells, and any other artifacts can be counted if desired and classified as rare, few, moderate, or many. The Table below provides recommended limits for these categories.

| Wet Prep (concentration) Enumeration | | |
|---|---|---|
| | Protozoa (#/20 40X fields) | Helminth (#/22x40 coverslip) |
| Rare | <4 | <4 |
| Few | 4-6 | 4-6 |
| Moderate | 6-20 | 6-20 |
| Many | >20 | >20 |

For yeast, 1-3 per hpf constitutes a rare number; 4-5 per high powered fielf constitutes few; 6-10 per hpf constitutes a moderate number; and >10 per hpf constitutes many.

Other parasites that can be assessed in the context of the present methods include *Giardia* and *Cryptosporidium*. These organisms can be detected in a variety of ways, including enzyme immunoassay (EIA) for specific antigens (e.g., GSA 65 and CSA) present in aqueous extracts of human stool samples. More specifically, one can employ the ProspecT® microplate assay according to the manufacturer's instructions to simultaneously detect GSA 65 and CSA. Briefly, stool specimens are added to break-away microplate wells to which anti-GSA 65 and anti-CSA antibody are bound. The antibodies are conjugated to an enzyme that later produces a detectable product when bound by an antigen. After unbound material is washed away, an enzyme substrate (TMB where the enzyme is horseradish peroxidase) is added to the well. In a positive reaction, the development of color indicates that parasitic antigens are present in the sample. In a negative reaction, antigen is either absent or present in insufficient amounts to be detected, and no colored reaction product develops. Acceptable samples include unpreserved stool, stool samples in Cary-Blair medium, SAF medium, or 10% formalin. Ideally, fresh samples have been frozen, samples in Cary-Blair medium are refrigerated (2-8° C.) and tested within one week of collection, and samples in SAF, 10% formalin or MF transport media are refrigerated or stored at room temperature and tested within two months. Stool samples treated with PVA are not acceptable for testing.

Similar assays can be configured to detect other antigens so long as an antigen-specific binding protein (e.g., an antibody) is available. For example, the ProspecT® *Entamoeba histolytica/dispar* microplate assay is available for the detection of EHSA (*E. histolytica* specific antigen).

In assays such as the ProspecT® assay, acceptable samples include unpreserved stool, stool samples in Cary-Blair medium, SAF medium, or 10% formalin.

Any of the methods described herein can include a step of identifying a patient who is a candidate for evaluation. In some cases, a physician or other healthcare provider may suspect giardiasis, caused by *Giardia lamblia*, or cryptosporidiosis, which is caused by *Cryptosporidium* sp. *G. lamblia* are transmitted via ingestion of viable cysts, and this occurs more frequently among children and in groups of people who live in close quarters. The acute stage occurs about 12-20 days after ingestion and typically lasts only a few days. The patient may complain of diarrhea and flatulence without the presence of blood in the stool or other hallmarks of inflammatory bowel disease. Malaise, malabsorption, anorexia, abdominal cramping, weight loss, and general weakness are some of the other manifestations of infection. The disease can linger for weeks or months as a chronic presentation.

Cryptosporidiosis is a serious intestinal disease that is commonly observed in people who work with young children, animal handlers, and travelers, and it is particularly dangerous to individuals who are immunosuppressed or otherwise weakened or compromised. Symptoms include diarrhea, abdominal pain, nausea and vomiting, fever, malaise and respiratory problems, which may last from several days to more than a month.

Any of the methods described herein can include a step in which the results of one or more of the assays described herein are correlated with patient symptoms and any other clinically relevant information.

EXAMPLES

Example 1

A 32 year-old male patient presents with abdominal discomfort and alterations in bowel movements (3-4 times/month) since returning from traveling in Nepal six months earlier. He has been evaluated for parasites at a local hospital. An EIA for *Entamoeba histolytica* was negative. He has difficulty when eating sweets or other sugar-rich foods, which leads to an urge to use the bathroom. The patient presented to a doctor who suspected Irritable Bowel Syndrome. While the doctor was concerned about the potential underlying causes of pain and discomfort, hospitalization and colonoscopy were not considered necessary at that time. The doctor elected to perform stool testing to evaluate digestion, inflammation, infection, and gut microflora. The following results were noted:

Pancreatic Elastase=188 (nl>200)
Calprotectin=22 (nl<50)
Eosinophilic Protein X=8.9 (nl<7.0)
Microscopy—positive for *Blastocystis hominis*

The patient was prescribed pancreatic enzymes with meals, treated with a prescription anti-parasitic agent, and offered L-glutamine to support healing of the gastrointestinal lining. Within one week, the patient began to experience improvement in symptoms he had experienced for the previous six months. L-Glutamine was continued for six weeks, and pancreatic enzymes were continued for three months, as were supplemental probiotics.

After three months, the symptoms had completely resolved and medications could be ceased. The patient remains symptom-free more than one year from the initial visit.

Example 2

A 42 year old female presents with a three year history of irregular bowel movements and intermittent lower abdominal pain, for which she has seen her previous primary care provider many times. She also has been diagnosed with depression and is currently using an SSRI for depression. She notes that the tri-cyclic anti-depressant she used previously did not significantly affect her abdominal pain. She has used fiber, anti-diarrheals, probiotics, and dietary changes in the past, to no avail.

Upon presentation the doctor chooses to run a stool test to evaluate the root cause of this illness. While waiting for the stool test to return, empiric use of probiotics at 10 billion cfu per day has made no difference.

Upon testing, pancreatic elastase was determined to be 482 (nl>200). At this level, one would conclude that the patient has normal pancreatic function and no need for pancreatic enzyme support. Calprotectin was determined to be 286 (nl<50). This level of elevation indicates severe gastrointestinal tract inflammation and warrants referral to a specialist for further investigation (i.e., colonoscopy). There was no evidence of parasite infection or altered gut flora.

While no clinical intervention is indicated, the patient was referred for colonoscopy for inflammatory changes in the gastrointestinal tract. She is diagnosed with ulcerative colitis and placed on steroids and 5-ASA. About 1-10% of patients with IBS go on to develop IBD. The stool test, with its use of a stool-based marker for GI inflammation, allowed for early detection and appropriate referral of this patient to the gastroenterologist. Subsequent evaluations of GI inflammation with the calprotectin biomarker can be used to monitor mucosal healing and determine if repair is sufficient or complete.

Example 3

A 21 year old female presents with a history of intermittent recurrent abdominal cramping, bloating/gas and occasional diarrhea over the past two years. She has been evaluated by her college health clinic on numerous occasions, was told that her symptoms were primarily 'stress related,' and was advised to cut back on her coffee intake during the day. She was recently evaluated for complaints of fatigue, and was diagnosed with hypothyroidism (including elevated thyroid antibodies) for which she is being treated. While home during a break, the patient was asked to do a stool analysis by her primary care doctor who was concerned that some underlying etiology had not been determined. Results were significant for the following:

Pancreatic Elastase=150 (nl>200)
   At this level, the pancreatic elastase clinically indicates moderate pancreatic insufficiency and need for pancreatic enzyme support. Evaluation of the underlying cause of pancreatic insufficiency is warranted.

Calprotectin=22 (nl<50)

A normal Calprotectin level indicates no inflammation due to neutrophilic activity in the gastrointestinal tract.

Eosinophil Protein X=13.1 (nl<7.0)

An elevated Eosinophil Protein X may be associated clinically with Celiac disease, parasitic infections, and/or IgE mediated food allergies.

Microscopy—no evidence of parasite infection or altered gut flora.

Given that Celiac disease can be consistent with the patient's clinical symptoms, and may be indicated on stool analysis by an elevated Eosinophil Protein X and compromised pancreatic exocrine function (low Pancreatic Elastase), the doctor decided to evaluate the patient for Celiac disease. Blood serologies (positive Tissue Transglutaminase IgA and positive anti-Endomysial antibody) confirmed the diagnosis of Celiac disease. The patient was placed on a gluten-free diet and given pancreatic digestive enzyme support. At follow-up, the patient reported that her symptoms had markedly improved—appearing only during times of dietary indiscretion.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising a plurality of tests to assist with the diagnosis of irritable bowel syndrome (IBS), the method comprising:

(a) providing a stool sample from a patient; and
   (b) subjecting the sample to an evaluation of (i) an elastase that is produced by the pancreas and remains detectable in the stool following passage through the intestine, (ii) calprotectin, and (iii) gut flora, wherein levels of the elastase less than about 350 µg/gram of stool, levels of calprotectin less than about 120 µg/gram of stool, and insufficient levels of beneficial gut flora indicate a diagnosis of IBS.

2. The method of claim 1, wherein the evaluation of gut flora comprises an evaluation of bifidobacteria species, *lactobacillus* species, and *Escherichia coli*.

3. The method of claim 1, further comprising testing for celiac disease, wherein the absence of celiac disease reinforces the diagnosis of IBS.

4. The method of claim 1, further comprising testing for occult blood in the stool sample, wherein the absence of occult blood reinforces the diagnosis of IBS.

5. The method of claim 1, wherein the method is performed and then repeated about six weeks later.

6. The method of claim 1, further comprising a step of identifying a patient as a candidate for testing.

7. The method of claim 6, wherein the patient is one complaining of abdominal pain, gas, bloating, constipation, or diarrhea.

8. The method of claim 1, wherein the level of the elastase is less than about 250 µg/gram of stool.

9. The method of claim 1, wherein the level of calprotectin is less than about 50 µg/gram of stool.

* * * * *